US011317825B2

(12) United States Patent
Mantri

(10) Patent No.: US 11,317,825 B2
(45) Date of Patent: May 3, 2022

(54) METHODS AND SYSTEMS FOR ENDOBRONCHIAL DIAGNOSIS

(71) Applicant: Pulmonx Corporation, Redwood City, CA (US)

(72) Inventor: Surag Mantri, Sunnyvale, CA (US)

(73) Assignee: Pulmonx Corporation, Redwood City, CA (US)

( * ) Notice: Subject to any disclaimer, the term of this patent is extended or adjusted under 35 U.S.C. 154(b) by 312 days.

(21) Appl. No.: 16/432,685

(22) Filed: Jun. 5, 2019

(65) Prior Publication Data

US 2019/0380619 A1 Dec. 19, 2019

Related U.S. Application Data

(60) Continuation of application No. 15/159,670, filed on May 19, 2016, now Pat. No. 10,314,516, which is a division of application No. 13/174,665, filed on Jun. 30, 2011, now Pat. No. 9,364,168.

(60) Provisional application No. 61/360,816, filed on Jul. 1, 2010.

(51) Int. Cl.
*A61B 5/087* (2006.01)
*A61B 5/00* (2006.01)
*A61B 5/091* (2006.01)

(52) U.S. Cl.
CPC .............. *A61B 5/087* (2013.01); *A61B 5/091* (2013.01); *A61B 5/6853* (2013.01)

(58) Field of Classification Search
CPC ........ A61B 5/087; A61B 5/091; A61B 5/6853
USPC ................................................. 600/529–534
See application file for complete search history.

(56) References Cited

U.S. PATENT DOCUMENTS

| 4,351,344 | A | 9/1982 | Stenzler |
|---|---|---|---|
| 7,798,147 | B2 | 9/2010 | Hendricksen et al. |
| 7,883,471 | B2 | 2/2011 | Aljuri et al. |
| 8,136,526 | B2 | 3/2012 | Perkins et al. |
| 9,364,168 | B2 | 6/2016 | Mantri |
| 10,314,516 | B2 | 6/2019 | Mantri |

(Continued)

FOREIGN PATENT DOCUMENTS

WO    WO-2009135070 A1    11/2009

OTHER PUBLICATIONS

Dernevik, et al. "Initial experience with the world's first digital drainage system. The benefits of recording air leaks with graphic representation," Dec. 27, 2006, European Journal of Cardio-Thoracic Surgery, 31, p. 209-213. (Year: 2007).*

(Continued)

*Primary Examiner* — Daniel L Cerioni
*Assistant Examiner* — Raymond P Dulman
(74) *Attorney, Agent, or Firm* — Wilson Sonsini Goodrich & Rosati

(57) ABSTRACT

A method of diagnosing an air leak in a lung compartment of a patient may include: advancing a diagnostic catheter into an airway leading to the lung compartment; inflating an occluding member on the catheter to form a seal with a wall of the airway and thus isolate the lung compartment; measuring air pressure within the lung compartment during multiple breaths, using the diagnostic catheter; displaying the measured air pressure as an air pressure value on a console coupled with the diagnostic catheter; and determining whether an air leak is present in the lung compartment based on the displayed air pressure value during the multiple breaths.

7 Claims, 4 Drawing Sheets

(56) References Cited

U.S. PATENT DOCUMENTS

| | | | |
|---|---|---|---|
| 2003/0051733 A1 | 3/2003 | Kotmel et al. | |
| 2006/0264772 A1* | 11/2006 | Aljuri | A61B 5/7278 600/538 |
| 2007/0142742 A1 | 6/2007 | Aljuri et al. | |
| 2007/0185406 A1* | 8/2007 | Goldman | A61B 5/08 600/533 |
| 2008/0027343 A1 | 1/2008 | Fields et al. | |
| 2011/0071415 A1* | 3/2011 | Karwoski | A61L 29/08 600/529 |
| 2011/0201956 A1 | 8/2011 | Alferness et al. | |

OTHER PUBLICATIONS

Dernevik, et al. Initial experience with the world's first digital drainage system. The benefits of recording air leaks with graphic representation. Eur J Cardiothorac Surg. Feb. 2007;31(2):209-13. Epub Dec. 27, 2006.
Notice of allowance dated Feb. 17, 2015 for U.S. Appl. No. 13/174,665.
Office action dated Jan. 27, 2015 for U.S. Appl. No. 13/174,665.
Office action dated Apr. 21, 2014 for U.S. Appl. No. 13/174,665.
Office action dated Sep. 21, 2018 for U.S. Appl. No. 15/159,670.
Office action dated Oct. 8, 2013 for U.S. Appl. No. 13/174,665.

* cited by examiner

METHODS AND SYSTEMS FOR ENDOBRONCHIAL DIAGNOSIS

CROSS-REFERENCE TO RELATED APPLICATION

This application is a continuation of U.S. patent application Ser. No. 15/159,670, filed May 19, 2016, now U.S. Pat. No. 10,314,516, which is a divisional of U.S. patent application Ser. No. 13/174,665, filed Jun. 30, 2011, now U.S. Pat. No. 9,364,168, which claims priority under 35 U.S.C. § 119(e) as a non-provisional application of U.S. Provisional Patent Application Ser. No. 61/360,816, entitled Methods and Systems for Endobronchial Diagnosis, filed Jul. 1, 2010, the full disclosures of which are hereby incorporated by reference.

BACKGROUND OF THE INVENTION

1. Field of the Invention

This invention relates generally to methods for diagnosis and treatment of lung disease.

2. Description of the Related Art

Chronic obstructive pulmonary disease (COPD), including emphysema and chronic bronchitis, is a significant medical problem currently affecting around 16 million people in the U.S. alone (about 6% of the U.S. population). In general, two types of diagnostic tests are performed on a patient to determine the extent and severity of COPD: 1) imaging tests; and 2) functional tests. Imaging tests, such as chest x-rays, computerized tomography (CT) scans, Magnetic Resonance Imaging (MRI) images, perfusion scans, and bronchograms, provide a good indicator of the location, homogeneity and progression of the diseased tissue. However, imaging tests do not provide a direct indication of how the disease is affecting the patient's overall lung function and respiration. Lung function can be better assessed using functional testing, such as spirometry, plethysmography, oxygen saturation, and oxygen consumption stress testing, among others. Together, these imaging and functional diagnostic tests are used to determine the course of treatment for the patient.

One of the emerging treatments for COPD involves the endoscopic introduction of endobronchial occluders or endobronchial one-way valve devices ("endobronchial valves" or "EBVs") into pulmonary airways to cause atelectasis (i.e., collapse) of a diseased/hyperinflated lung compartment, thus reducing the volume of that lung portion and allowing healthier lung compartments more room to breathe and perhaps reducing pressure on the heart. Examples of such a method and implant are described, for example, in U.S. patent application Ser. No. 11/682,986 and U.S. Pat. No. 7,798,147, the full disclosures of which are hereby incorporated by reference. One-way valves implanted in airways leading to a lung compartment restrict air flow in the inhalation direction and allow air to flow out of the lung compartment upon exhalation, thus causing the adjoining lung compartment to collapse over time. Occluders block both inhalation and exhalation, also causing lung collapse over time.

It has been suggested that the use of endobronchial implants for lung volume reduction might be most effective when applied to lung compartments which are not affected by collateral ventilation. Collateral ventilation occurs when air passes from one lung compartment to another through a collateral channel rather than the primary airway channels. If collateral airflow channels are present in a lung compartment, implanting a one-way valve or occluder might not be as effective, because the compartment might continue to fill with air from the collateral source and thus fail to collapse as intended. In many cases, COPD manifests itself in the formation of a large number of collateral channels caused by rupture of alveoli due to hyperinflation, or by destruction and weakening of alveolar tissue.

An endobronchial catheter-based diagnostic system typically used for collateral ventilation measurement is disclosed in U.S. Patent Publication No. 2003/0051733 (hereby incorporated by reference), wherein the catheter uses an occlusion member to isolate a lung segment and the instrumentation is used to gather data such as changes in pressure and volume of inhaled/exhaled air. Current state of the art methods for collateral ventilation measurement are disclosed in U.S. Pat. No. 7,883,471 and U.S. Patent Publication Nos. 2008/0027343 and 2007/0142742 (all of which are hereby incorporated by reference), in which an isolation catheter is used to isolate a target lung compartment and pressure changes therein are sensed to detect the extent of collateral ventilation. The applications also disclose measurement of gas concentrations to determine the efficiency of gas exchange within the lung compartment. Similar methods are disclosed in PCT Application No. WO2009135070A1 (hereby incorporated by reference), wherein gas concentration changes in a catheter-isolated lung portion allow collateral ventilation to be determined.

In addition to assessing collateral ventilation, there is an unmet need for quantifiably assessing air leaks (pneumothorax) within the lung. The lung is surrounded by a pleural cavity that ordinarily maintains a pressure that is slightly negative compared to atmospheric pressure. This slight negative pressure helps the lung inhale air from the atmosphere. An air leak occurs when a portion of the lung starts to leak air into the pleural cavity, thus removing the normal, negative pressure in the cavity and often leading to collapse of the lung. Such an air leak is caused by multiple factors such as disease, trauma to the lung, or as a complication of medical treatment.

Traditional methods of measuring air leaks have focused on a purely qualitative analysis of whether a leak exists rather than quantitative measures of the amount of leakage. Furthermore, the existing methods often rely on invasive means for diagnosis. For example, a Pleur-Evac® system (available from Teleflex Medical, www.teleflexmedical.com) relies on obtaining air from the pleural cavity via a catheter implanted into the pleural space via the chest. The air thus obtained from the pleural cavity is allowed to bubble through a fluid, and the quantity of the bubbles is correlated to the extent of the leak within the cavity. Such a method is inaccurate for multiple reasons. Since the value is obtained from the pleural cavity as a whole, there is no indication of where the air leak is located. The system also does not indicate the impact of the air leak on important parameters of lung function such as pressure or flow. Finally, the Pleur-Evac® system also does not indicate whether there are multiple air leaks and the rate of contribution of each air leak to the whole.

Therefore, a need exists for a more accurate and complete diagnostic method for quantifying air leaks within the lung. As discussed above, a need also exists for improved methods and systems to determine the presence of collateral channels and/or collateral ventilation. At least some of these objectives will be met by the embodiments described further below.

SUMMARY OF THE INVENTION

In one aspect of the present invention, a method of diagnosing an air leak in a lung compartment of a patient may involve: advancing a diagnostic catheter into an airway leading to the lung compartment; inflating an occluding member on the catheter to form a seal with a wall of the airway and thus isolate the lung compartment; measuring air pressure within the lung compartment during multiple breaths, using the diagnostic catheter; displaying the measured air pressure as an air pressure value on a console coupled with the diagnostic catheter; and determining whether an air leak is present in the lung compartment based on the displayed air pressure value during the multiple breaths.

In some embodiments, the console displays multiple air pressure values measured during the multiple breaths as a wave-form. In one embodiment, the console may display a wave-form displaying a base-line value. In one embodiment, a negative base-line value may be correlated with a size of an air leak. In some embodiments, the method may further include displaying on the console whether the air leak is present in the compartment. In some embodiments, the lung compartment may be a lobe of a lung, while in alternative embodiments the lung compartment may be a segment of a lung.

Optionally, some embodiments of the method may further involve using the diagnostic catheter to assess whether there is collateral ventilation into the lung compartment and determining a treatment method based on the determinations of the air leak and collateral ventilation. Some embodiments may further involve measuring air flow out of the lung compartment during the multiple breaths, using the catheter, and displaying the measured air flow as an air flow value. In such embodiments, the determining step may be based on the air pressure value and/or the air flow value. Any of the methods may be repeated to assess multiple lung compartments.

In another aspect of the present invention, a method of diagnosing an air leak in a lung compartment of a patient may include: advancing a diagnostic catheter into an airway leading to the lung compartment; inflating an occluding member on the catheter to form a seal with a wall of the airway and thus isolate the lung compartment; measuring air flow out of the lung compartment during multiple breaths, using the diagnostic catheter; displaying the measured air flow as an air flow value on a console coupled with the diagnostic catheter; and determining whether an air leak is present in the lung compartment based on the displayed air flow value during the multiple breaths.

In one embodiment, the measuring step may involve measuring air flow during inspiration and expiration. In such an embodiment, the determining step may include comparing air flow during inspiration to air flow during expiration. The determining step may optionally also include calculating a ratio of inspiration air flow to expiration air flow. In some embodiments, the method may further include estimating a size of the air leak based on the ratio. Also optionally, the method may further involve displaying on the console whether an air leak is present.

These and other aspects and embodiments of the present invention are set forth in further detail below, in reference to the attached drawings.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE INVENTION

Although the detailed description contains many specifics, these should not be construed as limiting the scope of the invention but merely as illustrating different examples and aspects of the invention. Various modifications, changes and variations may be made in the disclosed embodiments without departing from the spirit and scope of the invention.

The present application provides methods and systems for targeting, accessing and diagnosing diseased lung compartments. Such compartments may be an entire lobe, a segment, a sub-segment or any such portion of the lung. In the disclosed embodiments, lung functionality is assessed by isolating a lung compartment to obtain various measurements. Though COPD is mentioned as an example, the applicability of these methods for treatment and diagnosis is not limited to COPD, but can be applicable to any lung disease.

The methods are minimally invasive in the sense that the required instruments are introduced orally, and the patient is allowed to breathe normally during the procedures. The methods involve detecting the presence or characteristics (e.g., concentration or pressure) of one or more naturally occurring or introduced gases to determine the presence of collateral ventilation, or may involve measurement of oxygen saturation of tissue.

Figure 1:
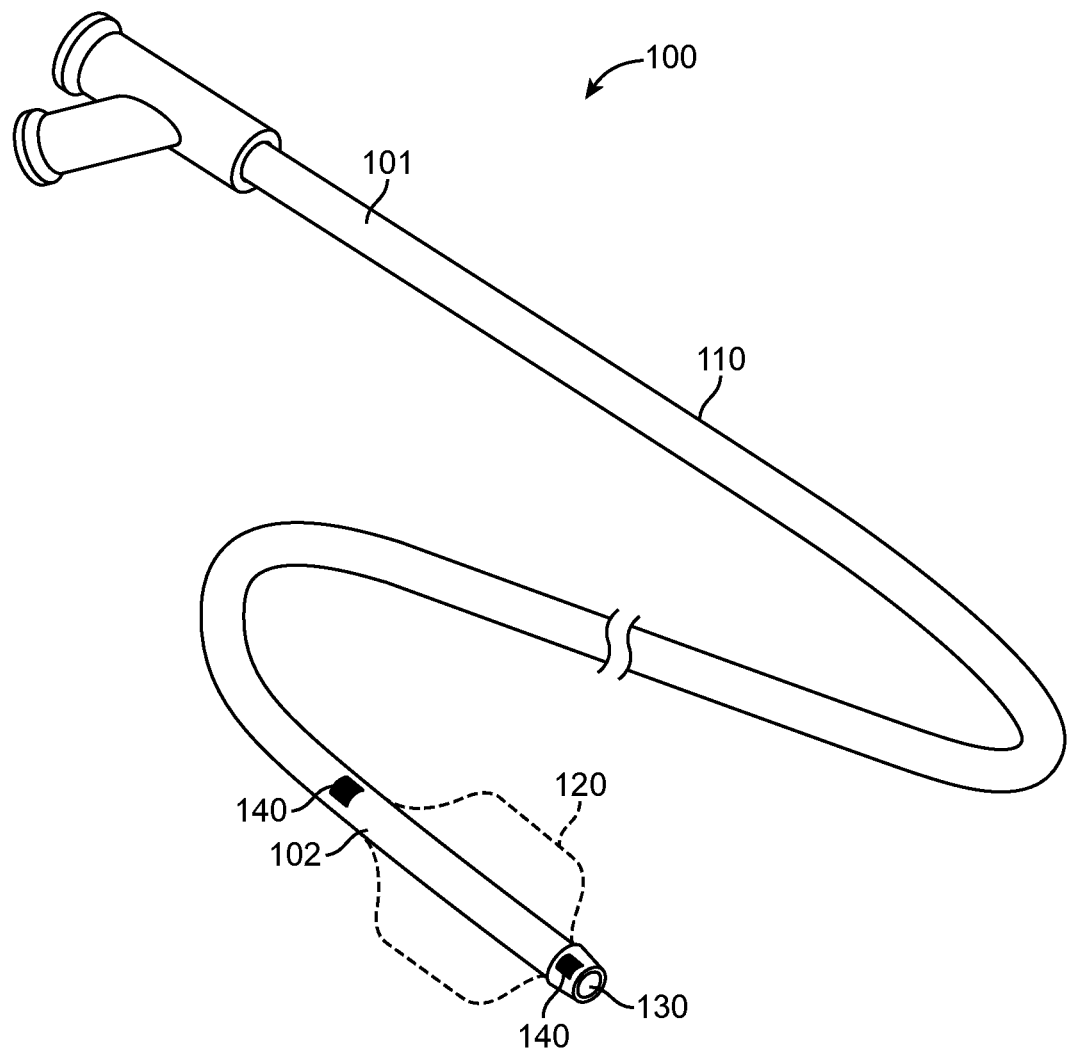
FIG. 1 shows a diagnostic or assessment catheter used in methods according to one embodiment of the present invention.
Figure 2:
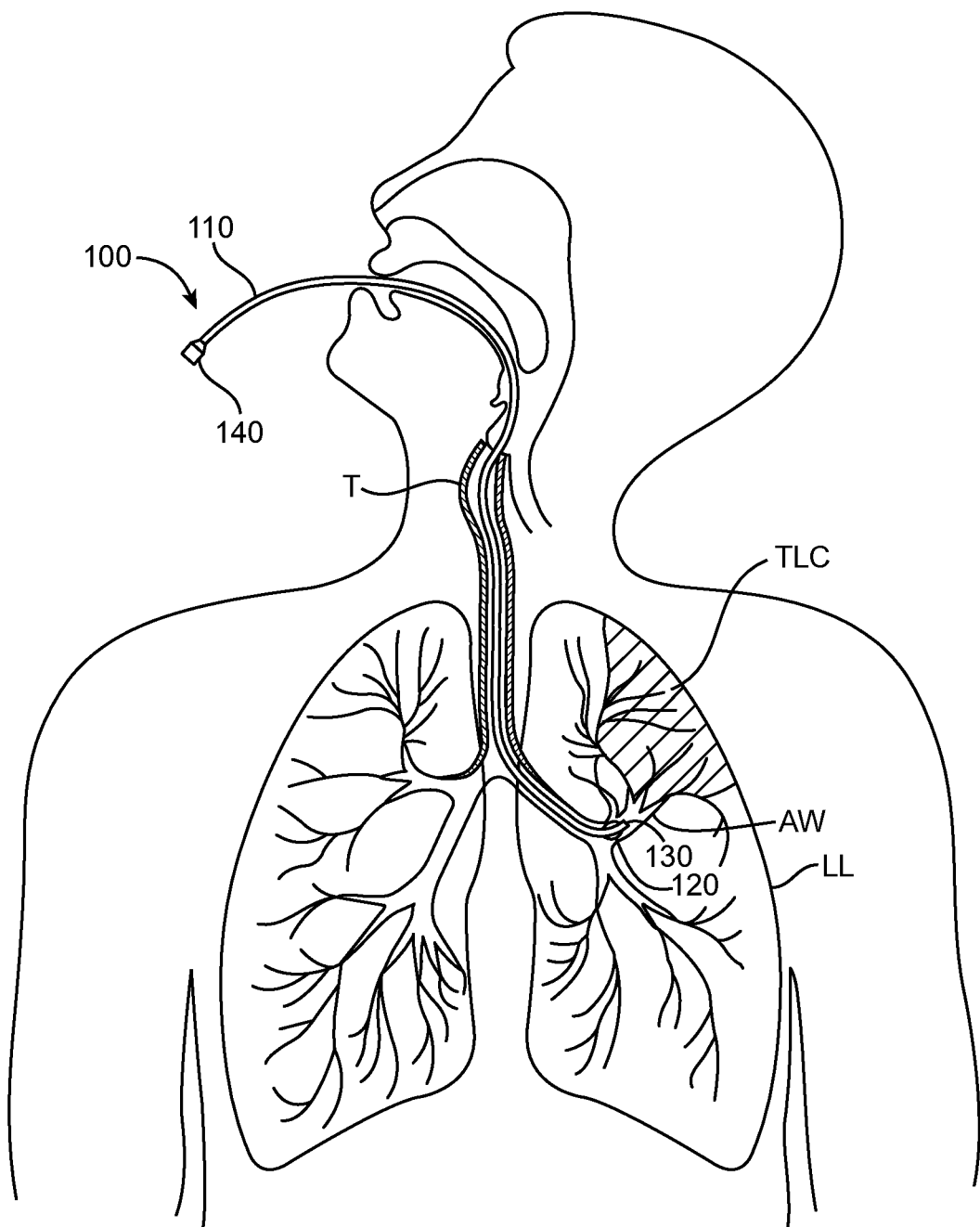
FIG. 2 shows the placement of the catheter shown in FIG. 1 in the lung according to one embodiment.

In some embodiments, isolation of the lung comprises sealingly engaging a distal end of a catheter in an airway feeding a lung compartment, as shown in FIGS. 1 and 2. Such a catheter has been disclosed in co-pending published U.S. patent application Ser. No. 10/241,733, which is incorporated herein by reference. As shown in FIG. 1, the catheter 100 comprises a catheter body 110, and an expandable occluding member 120 on the catheter body. The catheter body 110 has a distal end 102, a proximal end 101, and at least one lumen 130, extending from a location at or near the distal end to a location at or near the proximal end.

The proximal end of catheter 100 is configured to be coupled with an external control unit (or "console," not shown), and optionally comprises an inflation port (not shown). The distal end of catheter 100 is adapted to be advanced through a body passageway such as a lung airway. The expandable occluding member 120 is disposed near the distal end of the catheter body and is adapted to be expanded in the airway which feeds the target lung compartment. In one embodiment, the occluding member 120 is a compliant balloon made of transparent material. The transparent material allows visualization using the bronchoscope through the balloon. The occluding member 120 is inflatable via a syringe that is configured to be coupled to the inflation port. Optionally, catheter 100 comprises visual markers at the proximal and distal ends of the balloon to identify the location of the occluding member 120 within the airway prior to inflation. The occluding member 120 material inflates and seals with inflation pressures between 5-20 psi to prevent balloon migration within the airway. This inflation pressure also aids the occluding member 120 in maintaining a symmetrical configuration within the airway, thereby ensuring that the catheter (which is centered within the occluding member 120) will remain centered within the airway. The occluding member 120 material and attachment are also configured to minimize longitudinal movement of the occluding member 120 relative to the catheter body 110 itself. To accommodate the higher inflation pressure, the occluding member 120 is made of a polyurethane such as Pellethane 80A, but can be made of any material that is configured to maintain structural integrity at a high inflation pressure.

Additionally and optionally, catheter 100 may further comprise at least one gas sensor 140 located within or in-line with the lumen 130 for sensing characteristics of various gases in air communicated to and from the lung compartment. The sensors may comprise any suitable sensors or any combination of suitable sensors, and are configured to communicate with control unit 200. Some embodiments of sensors include pressure sensors, temperature sensors, air flow sensors, gas-specific sensors, or other types of sensors. As shown in FIG. 1, the sensors 140 may be located near the distal end 102 of the catheter 100. Alternatively, the sensors 140 may be located at any one or more points along the catheter 100, or in-line with the catheter 100 and within the control unit with one or more measuring components.

As shown in FIG. 2, at least a distal portion of the catheter body 110 is adapted to be advanced into and through the trachea (T). The catheter may optionally be introduced through or over an introducing device such as a bronchoscope. The distal end 102 of the catheter body 110 can then be directed to a lung lobe (LL) to reach an airway (AW) which feeds a target lung compartment (TLC), which is to be assessed. When the occluding member 120 is expanded in the airway, the corresponding compartment is isolated with access to and from the compartment provided through the lumen 130.

Figure 3:
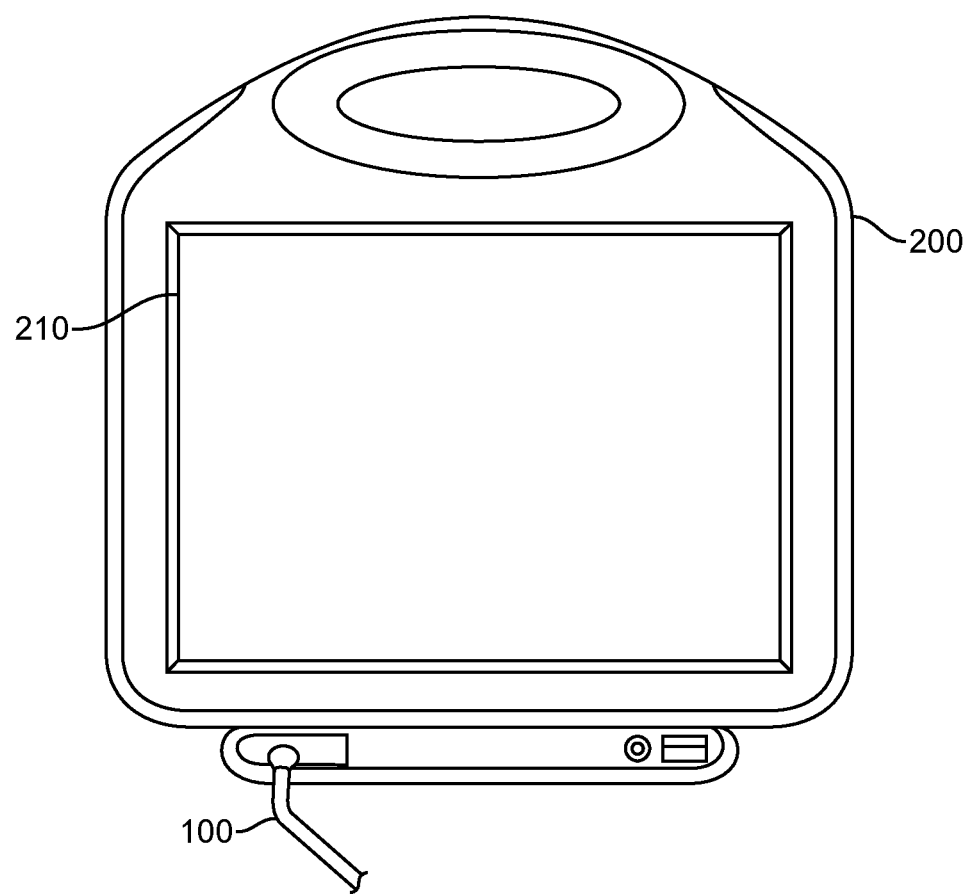
FIG. 3 shows a console configured to receive the catheter shown in FIG. 1 according to one embodiment.

Referring now to FIG. 3, the proximal end of the catheter 100 may be configured to be coupled with a control unit (or "console") 200. The control unit 200 comprises one or more measuring components (not shown) to measure lung functionality. The measuring components may take many forms and may perform a variety of functions. For example, the components may include a pulmonary mechanics unit, a physiological testing unit, a gas dilution unit, an imaging unit, a mapping unit, a treatment unit, a pulse oximetry unit or any other suitable unit. The components may be disposed within the control unit 200, or may be attached to the unit 200 from an external source. The control unit 200 comprises an interface for receiving input from a user and a display screen 210. The display-screen 210 will optionally be a touch-sensitive screen, and may display preset values. Optionally, the user will input information into the control unit 200 via a touch-sensitive screen mechanism. Additionally and optionally, the control unit 200 may be associated with external display devices such as printers or chart recorders. At least some of the above system embodiments will be utilized in the methods described below.

Assessment of Pleural Air Leak in Patients. One diagnostic test that can be undertaken using the above system is the measurement of air leaks from the lung into the pleural cavity. In order to do this, the catheter is introduced into a lung compartment, as shown in FIG. 2, and the pressure is measured. An unusually negative pressure indicates the presence of an air leak.

To begin, catheter 100 is placed into an airway leading to a target lung compartment (TLC) and the occluding member 120 is inflated to isolate the TLC. Thereafter, negative pressure within the TLC is monitored. If the negative pressure becomes increasingly negative over time, this may indicate that there is a leak into the pleural cavity from another lung compartment. If a strong and consistent negative pressure is observed, this indicates an air leak within the TLC being tested.

Figure 4:
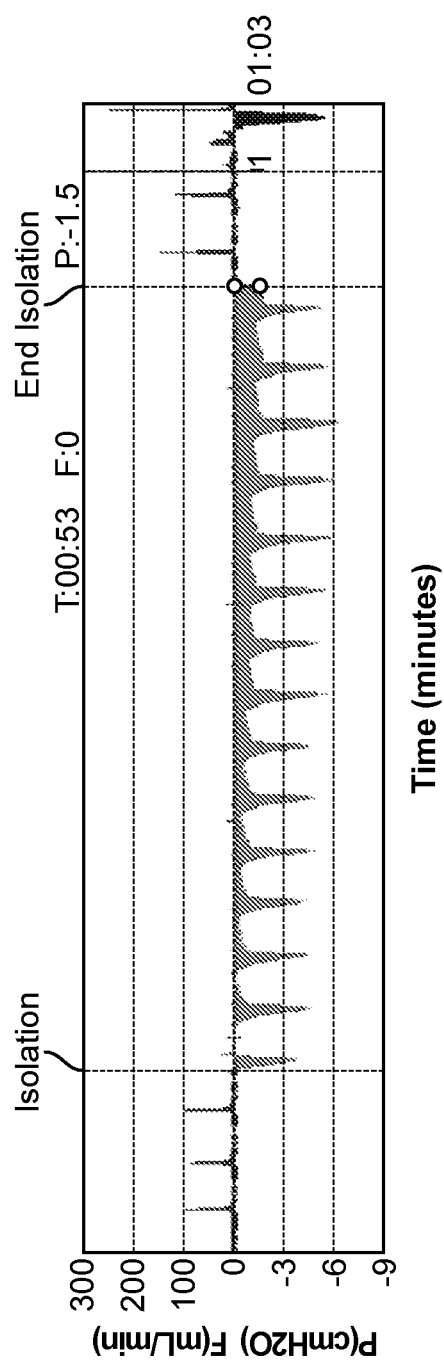
FIG. 4 shows a graph indicating an air leak according to one embodiment.
Figure 5:
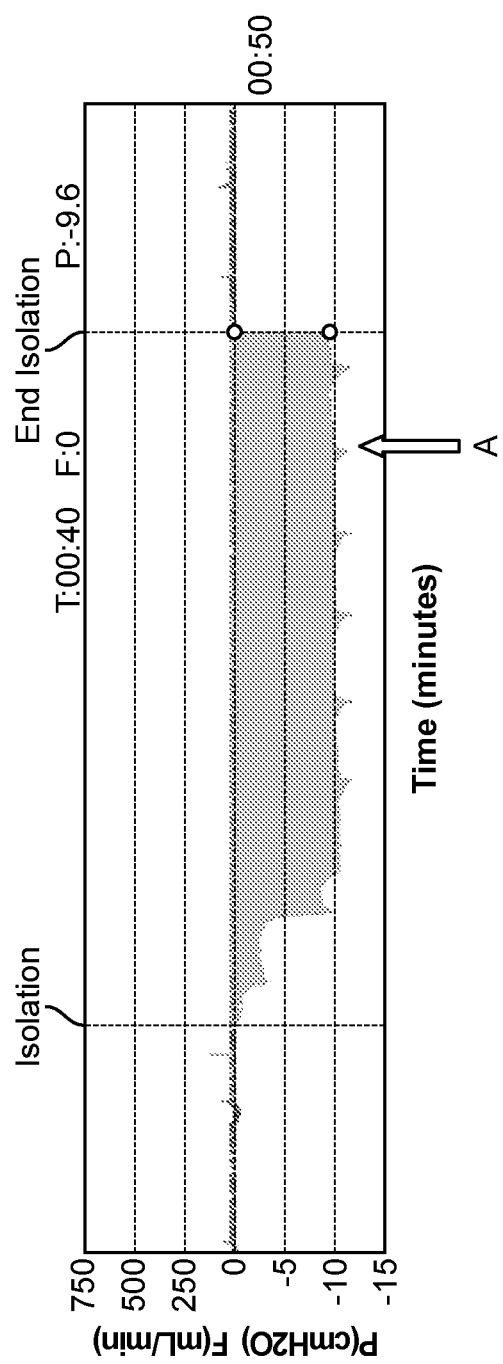
FIG. 5 shows a graph showing the presence of an air leak.

FIGS. 4 and 5 show exemplary graphs of the above as they would be displayed on the console 200 during a test. In FIG. 4, after occlusion by the occluding member, it is apparent that negative pressure readings are recorded. This in itself is normal, as during regular breathing negative pressure builds during inhalation and reduces during exhalation. Negative pressure during inhalation would thus be expected in a normal lung compartment. However, as apparent in FIG. 4, there is a trend towards greater negative pressure within the compartment over time. This indicates that there may be another source of negative pressure within the lung, for example in an adjacent lung lobe or segment. FIG. 4 thus is a representative graph of a suspected air leak in an adjoining lung compartment. If encountered, a user would study one or more adjacent compartments for the presence of an air leak.

In contrast, FIG. 5 is an example of a pressure graph showing the resulting wave-form from a lung compartment in which an air leak is present. As apparent in the graph, after isolation, the pressure becomes negative relatively quickly and maintains a very low negative baseline during the course of the test when the compartment remains isolated. Respiration is still being recorded, as there are still inflections in the wave-form (denoted by the arrow 'A') as inhalation occurs. This phenomenon occurs because the leak allows the pressure within the compartment to normalize with the natural negative pressure of the pleural cavity.

Once an air leak has thus been identified, it is easily quantified by referring to the baseline value of the negative pressure. A smaller air leak creates less negative pressure and thus displays a greater baseline value than a larger air leak.

Additionally or alternatively, flow may be monitored to determine the presence and extent of an air leak. If a normal lung is isolated such that only exhalation is recorded through the catheter, positive flow increases during exhalation and is reduced to zero during inhalation. If an air leak exists, during flow monitoring, the graphs on the console display a sudden increase in flow, followed by a gradual drop. If both inspiratory and expiratory flows are followed, wherever the leak exists, a higher ratio of inspiratory to expiratory flow is expected than would be seen in a normal lung compartment. This is due to the fact that during inspiration, greater flow exists as the pressure within the pleural space draws more air from the compartment. Furthermore, the magnitude of the flow ratio indicates the magnitude of the leak, with a greater ratio correlating to a more sizable leak.

Optionally, external sources may also be used to facilitate the testing. For example, the patient may be placed on a ventilator to ensure regulated airflow into the lung. Further, rather than using the console 200 at the proximal end of catheter 100, a manometer or a flow gauge may be used to determine flow rate. Further, the catheter 100, with or without console 200, may be used in conjunction with commercial systems such as the Pleur-Evac® system to improve the performance of those systems. For example, the catheter may be used to infuse a gas marker or colored gas into the lung compartment to allow for easy viewing in the Pleur-Evac® system. Further, the catheter may be used to speed healing by applying suction pressure to the affected lung compartment in the hopes of closing the air leak.

Once a diagnosis of an air leak has been made, a treatment plan may be determined. Since the size of the air leak is correlated with the time for the air leak to heal, information on the size of the air leak could be used to predict the length of time necessary for healing. Further, the region subject to the air leak may be sealed off from the rest of the lung using endobronchial valves or any other method. This would ensure that the surrounding lung compartments are not affected by the pressure differential caused by the air leak, while simultaneously allowing the air leak to heal over time.

Additionally, the diagnosis of an air leak may be combined with other diagnoses in order to more effectively treat the patient. For example, an air leak diagnosis may be combined with a diagnosis of collateral ventilation in order to determine a more accurate method of treatment. This is particularly useful because if a lung compartment with an air leak is subject to collateral ventilation, treatment by sealing the compartment alone would be insufficient, as air would escape through collateral channels into neighboring compartments. Thus, a diagnosis of collateral ventilation in conjunction with a diagnosis of air leak would allow identification of all the compartments that would need to be sealed in order to effectively contain the air leak. In some embodiments, the same methods described above for measuring pressure and/or flow within a lung compartment may be used to assess collateral ventilation in a compartment.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A method of diagnosing an air leak in a lung compartment of a patient, the method comprising:
   advancing a diagnostic catheter into an airway leading to the lung compartment;
   inflating an occluding member on the catheter to form a seal with a wall of the airway and thus isolate the lung compartment;
   externally applying suction pressure to a pleural cavity of the patient;
   measuring air pressure within the isolated lung compartment during multiple breaths, using the diagnostic catheter, wherein the measured air pressure does not maintain a negative baseline value during multiple breaths thus indicating that the lung compartment being measured is not communicating to the external suction pressure being applied to the pleural cavity;
   displaying the measured air pressure as an air pressure value on a console coupled with the diagnostic catheter; and
   determining that an air leak is not present in the lung compartment based on the displayed air pressure value during the multiple breaths.

2. The method of claim 1, further comprising advancing the diagnostic catheter into an additional airway leading to an additional lung compartment;
   inflating the occluding member on the catheter to form a seal with a wall of the additional airway and thus isolate the additional lung compartment;
   measuring air pressure within the isolated additional lung compartment during multiple breaths, using the diagnostic catheter;
   displaying the measured air pressure within the isolated additional lung compartment during the multiple breaths as an air pressure value on the console coupled with the diagnostic catheter; and
   determining whether an air leak is present in the additional lung compartment based on the displayed air pressure value during the multiple breaths.

3. The method of claim 1, wherein the console displays multiple air pressure values measured as a wave-form.

4. The method of claim 1, further comprising displaying on the console whether the air leak is present in the compartment.

5. The method of claim 1, wherein the lung compartment comprises a lobe of a lung.

6. The method of claim 1, wherein the lung compartment comprises a segment of a lung.

7. The method of claim 1, further comprising:
   using the diagnostic catheter to assess whether there is collateral ventilation into the lung compartment; and
   determining a treatment method based on the determinations of the air leak and collateral ventilation.

* * * * *